United States Patent [19]
Hornes et al.

[11] Patent Number: 5,512,439
[45] Date of Patent: Apr. 30, 1996

[54] OLIGONUCLEOTIDE-LINKED MAGNETIC PARTICLES AND USES THEREOF

[75] Inventors: Erik Hornes; Lars Korsnes, both of Oslo, Norway

[73] Assignee: Dynal AS, Oslo, Norway

[21] Appl. No.: 272,372

[22] Filed: Jul. 6, 1994

Related U.S. Application Data

[63] Continuation of Ser. No. 688,484, filed as PCT/EP89/01419, Nov. 21, 1989, abandoned.

[30] Foreign Application Priority Data

| Nov. 21, 1988 | [GB] | United Kingdom | 8827157 |
|---|---|---|---|
| Nov. 21, 1988 | [GB] | United Kingdom | 8827158 |
| Nov. 21, 1988 | [GB] | United Kingdom | 8827159 |
| Nov. 21, 1988 | [GB] | United Kingdom | 8827160 |
| Nov. 21, 1988 | [GB] | United Kingdom | 8827166 |
| Nov. 21, 1988 | [GB] | United Kingdom | 8827167 |
| Mar. 22, 1989 | [GB] | United Kingdom | 8906643 |

[51] Int. Cl.⁶ ............................. C12P 19/34; C12Q 1/68; G01N 33/553
[52] U.S. Cl. .................. 435/6; 435/91.1; 435/91.2; 435/91.5; 514/44; 436/526
[58] Field of Search ................ 435/6, 91.1, 91.2, 435/91.5; 514/44; 436/526

[56] References Cited

U.S. PATENT DOCUMENTS

| 4,654,267 | 3/1992 | Ugelstad et al. | |
| 4,672,040 | 6/1987 | Josephson | |
| 4,774,265 | 9/1988 | Ugelstad et al. | 521/55 |
| 4,775,619 | 10/1988 | Urdea | |

FOREIGN PATENT DOCUMENTS

| 0154505A2 | 9/1985 | European Pat. Off. |
| 0224126A2 | 6/1987 | European Pat. Off. |
| 0230768A1 | 8/1987 | European Pat. Off. |
| 0265244A2 | 4/1988 | European Pat. Off. |
| 0281390A3 | 7/1988 | European Pat. Off. |
| WO88/06632 | 9/1988 | WIPO |
| WO89/03674 | 5/1989 | WIPO |
| WO89/04373 | 5/1989 | WIPO |
| WO89/09282 | 10/1989 | WIPO |
| WO89/11546 | 11/1989 | WIPO |

OTHER PUBLICATIONS

Matijevic, E. Acc. Chem. Res. 14:22–29 (1981).
Chu et al. DNA 4(4) 327–331, 1985.
Nucleic Acids Research, vol. 16, No. 13, 1988, p. 6232, Atkinson et al.
Nucleic Acids Research, vol. 16, No. 7, pp. 3025–3028, Apr. 11, 1988, Stefan Stahl et al.
Chemical Abstracts, vol. 108, 1988, Monograph No. 201021e, Ugelstad et al.

*Primary Examiner*—W. Gary Jones
*Assistant Examiner*—Paul B. Tran
*Attorney, Agent, or Firm*—Foley & Lardner

[57] ABSTRACT

Monodisperse, superparamagnetic particles carrying a plurality of molecules of an oligonucleotide are disclosed and may be used inter alia for sequencing single-stranded nucleic acids. The oligonucleotide may be covalently attached or affinity bonded to the particles either by their 3' or 5' termini. The particles have a specific gravity in the range 1.1–1.8 and are 1–10 microns in diameter. A kit for the isolation or processing of target nucleic acid is also disclosed.

20 Claims, 2 Drawing Sheets

OLIGONUCLEOTIDE-LINKED MAGNETIC PARTICLES AND USES THEREOF

This application is a continuation of application Ser. No. 07/688,484, filed as PCT/EP89/01419, Nov. 21, 1989, now abandoned.

BACKGROUND OF THE INVENTION

1. Field of the Invention

This invention relates to novel nucleic acid probes and methods and kits for their preparation and use.

2. Background Information

In the biochemical manipulation of nucleic acids it is frequently desirable to isolate particular nucleic acid material from a complex mixture and to subject this to a wide variety of processes. It has been found particularly useful, where a sufficiently long sequence of the target nucleic acid is known, to design an oligonucleotide probe which will hybridise selectively to that sequence and which may then be used in the identification and/or isolation of the nucleic acid. In particular, it has been proposed to immobilise such a probe so that on contact with a complex mixture containing the target nucleic acid, the latter is selectively immobilised and may thus be separated.

It has been proposed to attach oligonucleotides to magnetic particles previously (for example in U.S. Pat. No. 4,672,040 of Advanced Magnetics, EP 265244 of Amoco Corporation). However, these have never been monodisperse and have normally comprised magnetite which has been ground to an appropriate average particle size and then coated with a substance providing functional groups permitting attachment of a range of biomolecules of interest including oligonucleotides. Furthermore, such magnetic particles have proved unreliable particularly in automated reaction systems, and have not found favour in practice. In particular, it has been found that fine magnetic particles produced by grinding often respond inadequately to magnetic aggregation so that a significant fraction remain in suspension, together with attached biomolecules and a less than quantitative isolation of the biomolecules is effected. The present invention is based on the finding that monodisperse, superparamagnetic particles are far more reliable than previously proposed magnetic particles.

SUMMARY OF THE INVENTION

According to the present invention we provide monodisperse, superparamagnetic particles carrying a plurality of molecules of an oligonucleotide.

The particles according to the invention may be used as probes for hybridisation to target single stranded nucleic acids or may serve to permit sequencing of the said oligonucleotide.

The oligonucleotide is preferably single stranded DNA since this will hybridise both to RNA and single stranded DNA and is much more stable than RNA. Such DNA includes oligo-dT, which which will hybridise with the poly A 'tails' universally present on native eukaryotic mRNA, and specific DNA sequences which hybridise with specific sequences in target RNA and ssDNA molecules or may be DNA molecules for sequencing. Each probe may consist of a directly attached single stranded DNA sequence which may be oligo-dT or a specific DNA sequence or it may be attached to the magnetic particle via a double stranded piece of DNA. The term 'oligonucleotide' as used herein includes both synthetic and native DNA and RNA sequences of any length.

The chain length of the oligonucleotide is preferably from 12 to 200 bases, more preferably 15–50 bases. The probe oligonucleotide, comprising the oligo(dT) sequence and, for certain applications, restriction enzyme site(s), may be most advantageously prepared by utilizing any of the commercially available DNA synthesis devices, e.g. those devices available from Applied Biosystems, Inc. (850-T Lincoln Center Drive, Foster City, Calif. 94404).

The probes according to the invention will in general be used in the isolation of target nucleic acids and their subsequent manipulation by chemical and/or biochemical techniques.

Several advantages of the use of magnetic particles stand out clearly. The magnetic particles can be added to a mixture containing the target nucleic acid, e.g. a cell extract, stirred and then magnetically drawn to one side of the receptacle. The liquid can then be removed together with unwanted components and the magnetic particles, having the RNA bound thereto, can then be redispersed in a washing solution. The washing step can be repeated several times in quick succession. The whole process of obtaining the target nucleic acid can be performed in under 15 minutes.

A further advantage is the ease with which hybridisation or any process effected using the magnetic particles can be continuously monitored by magnetically aggregating the particles at intervals and assaying a label associated either with the material on the particles or with material in the supernatant.

The use of magnetic aggregation to separate the particles is far less vigorous than traditional separation techniques such as centrifugation which generate shear forces which can degrade nucleic acids or proteins.

The particles are monodisperse and superparamagnetic and both these properties greatly assist the kinetics of reactions in which the particles are involved. It is a surprising feature of the invention that the probes carried by the particles react in the various reactions virtually as rapidly as if free in solution. Thus, for example, the total isolation of mRNA from a cell lysate using magnetic beads can be effected in about 15 minutes in contrast with the 2 hour period using an affinity column. By using monodisperse particles, that is particles of approximately the same size, the reaction rate and other parameters are particularly uniform. By using superparamagnetic particles (that is particles containing sub-particles of ferromagnetic material which are smaller than the domain size required to maintain permanent magnetism), one can avoid magnetic aggregation or clumping of the particles during reaction, thus again ensuring uniform and rapid reaction kinetics. Thus, the particles can readily be aggregated at a uniform speed onto a surface by application of a magnetic field but can readily be redispersed for a subsequent treatment step, e.g. by physical agitation. This uniformity of behaviour and rapidity of reaction lends itself particularly to automation, which is an essential requirement of many of the nucleic acid manipulations required in commercial production and/or repetitive processes. It is most important that the reactions and separations can be carried out completely reliably by an appropriate machine with minimal human intervention.

DESCRIPTION OF THE PREFERRED EMBODIMENTS

The preferred magnetic particles for use in this invention are monodisperse superparamagnetic beads produced according to EP 83901406.5 (Sintef), the disclosure of which is incorporated herein by reference. In these beads, the iron is very uniformly distributed and provides a very uniform response to a magnetic field which is important in designing a reproducible procedure, particularly for automation, since all the beads move at the same speed. Furthermore, since a reproducible amount of iron can be incorporated in each particle, this can be adjusted to a relatively low level which permits the specific gravity of the particles to be in the range specified below. In the case of prior, less regular products, small particles either had too little iron to counteract Brownian forces when a magnet was applied or the specific gravity of the material led to undesirable sedimentation of the larger particles. Some automated systems use magnetic fields to restrain the particles within a reaction zone while solutions are passed through; uniform magnetic and rheological properties are essential in magnetic particles for use in such a system.

The term "monodisperse" used herein is intended to encompass size dispersions having a diameter standard deviation of less than 5%.

We prefer to use beads having a specific gravity in the range 1.1 to 1.8 most particularly 1.2 to 1.5. In the monodisperse beads used in accordance with the invention, the specific gravity is, again, particularly uniform, leading to uniform and predictable kinetic characteristics.

Advantageously, the monodisperse particles are spherical beads of diameter at least 1 and preferably at least 2 microns, being preferably not more than 10 and more preferably not more than 6 microns in diameter e.g. about 3 microns. Smaller particles sediment more slowly and in some cases the sedimentation time may be long compared to the reaction time, thus avoiding the need for physical agitation. However, particles of mean diameter 0.1 to 1.5 microns including fine particles of much smaller diameter, as used in the prior art, behave unreliably in response to magnetisation.

The attachment of the probes to the particles may be by direct chemical bonding as well as affinity binding, by streptavidin/biotin complexes and the like.

For attachment of the probes, the magnetic particles may carry functional groups such as hydroxyl, carboxyl, aldehyde or amino groups. These may in general be provided by treating uncoated monodisperse, superparamagnetic beads, to provide a surface coating of a polymer carrying one of such functional groups, e.g. polyurethane together with a polyglycol to provide hydroxyl groups, or a cellulose derivative to provide hydroxyl groups, a polymer or copolymer of acrylic acid or methacrylic acid to provide carboxyl groups or an aminoalkylated polymer to provide amino groups. U.S. Pat. No. 4,654,267 describes the introduction of many such surface coatings.

Preferred coated particles for use in the present invention may be prepared by modification of the beads according to the U.S. Pat. Nos. 4,336,173, 4,459,378 and 4,654,267, the disclosure of which is incorporated herein by reference. Thus, for example, macroreticular porous polymer particles, prepared from styrene-divinylbenzene and with a diameter of 3.15 microns were treated with $HNO_3$ to introduce —$NO_2$ groups at the surface of the pores. Then the particles were dispersed in an aqueous solution of $Fe^{2+}$. The $FE^{2+}$ is oxidised by the —$NO_2$ groups which leads to precipitation of insoluble iron oxy-hydroxy compounds inside the pores. After heating the iron exists as finely divided grains of magnetic iron oxides throughout the volume of the porous particles. The $NO_2$ groups are reduced by the reaction with $Fe^{++}$ to $NH_2$ groups.

To fill up the pores and to introduce the desired functional groups at the surfaces, different monomers are caused to polymerize in the pores and at the surface. In the case of a preferred type of particle, the surface carries —OH groups connected to the polymeric backbone through —$(CH_2CH_2O)_{8-10}$ linkages. Other preferred beads carry —COOH groups obtained through polymerization of methacrylic acid.

Thus, for example, the $NH_2$ groups initially present in the beads may be reacted with a diepoxide as described in U.S. Pat. No. 4,654,267 followed by reaction with methacrylic acid to provide a terminal vinyl grouping. Solution copolymerisation with methacrylic acid yields a polymeric coating carrying terminal carboxyl groups as in R452 beads referred to below. Similarly, amino groups can be introduced by reacting a diamine with the above product of the reaction with a diepoxide as in the R240, R442 and R469 beads, while reaction with a hydroxylamine such as aminoglycerol introduces hydroxy groups as in the M450 and L255 beads.

DYNABEADS M450 (diameter 4.5 microns) which may be obtained from Dynal, Oslo, Norway have been coated with a monomeric epoxide, resulting in a mixture of epoxy and hydroxy groups. Contact with water however, converts the epoxy groups to hydroxy groups.

DYNABEADS M-280 (diameter 2.8 microns) are polystyrene beads having hydroxyl groups which have been converted into tosyloxy groups by reaction with p-toluene sulphonyl chloride.

Using functionalised coatings of the above types, we have found the non-specific binding of DNA and/or RNA to be very low, particularly in the case of the carboxylated beads.

Where the hybridised mRNA is to be used subsequently in cDNA synthesis, the probe and RE linker are preferably attached to the magnetic particles via carboxyl groups, the DNA being firstly provided with a 5'-terminal amino group which can be made to form an amide bond with the carboxyl using a carbodiimide coupling agent. 5'- attachment of DNA can also be effected using hydroxylated magnetic particles activated with CNBr to react with 5'- amino DNA.

The 3'-attachment of the oligonucleotide DNA can also be effected by chemical synthesis. Here again, the very uniform nature of the monodisperse particles provides uniform reaction rates particularly suited to synthesis in an automated synthesiser such as the GENE ASSEMBLER (Pharmacia AS). The magnetic particle needs to be provided initially with a hydroxyl or protected hydroxyl group. DYNABEADS M-280 of Dynal A/S are well suited to this purpose. If necessary, however, other surface functions such as carboxyl could be used to attach a linker carrying a hydroxyl group or alternatively a 3'-attached nucleotide.

5'-Attachment may be effected by coupling of 5'-aminooligonucleotides to tosyl-activated magnetic particles. The latter may be produced by tosylation of hydroxylated magnetic particles such as DYNABEADS M-280 of Dynal A/S. Displacement of the tosyloxy group leaves the 5'-amino group directly attached to the magnetic beads.

Where the probe is merely to be used for mRNA isolation, however, the 3' end of the probe may be attached to the magnetic particles and this may be conveniently effected by forming a phosphoramidate linkage between the 3'-phosphate grouping of the DNA and an amino group on the particle.

Since biotin labelled nucleotides are commercially available, the 3'- end of DNA fragments can easily be labelled using DNA polymerase and these may be conveniently bound to avidin or streptavidin attached to the magnetic particles e.g. via a hydroxy group. The biotin label may be attached to the nucleotide by a spacer arm, such as one or more ε-aminocaproic acid moieties, to minimize steric hindrance. Thus, for example, a double stranded plasmid may be cut at a restriction site and the end filled with biotinylated nucleotides, as providing biotin at the 3'-end of each strand. If the linearised plasmid is then cut at another RE site, a section of double stranded DNA is excised and may be attached to streptavidin coated beads. Removal of the non-biotinylated strand leaves a biotin-attached oligonucleotide attached to the beads.

In general, the functionalisation of the beads and subsequent attachment of probes is advantageously such that each magnetic particle carries $10^3$-$10^6$ probes. (1–300 pmols per mg). The uniform size of the magnetic particles is of advantage in ensuring uniform probe density when the probes are reacted with the particles. Uniform probe density is important in ensuring that all the probes behave in substantially the same way in the various procedures in which they are used.

It is a remarkable feature of the invention that enzyme activity appears to take place very close to the particle surface e.g. within 7 bases. Thus, if an RE site is present in a linker sequence as discussed hereinafter and if the probe is subsequently used as a primer, it is found that sscDNA and hence ds cDNA can be synthesised by the DNA polymerase past the RE site towards the bead surface and can thus itself readily be cleaved by the appropriate endonuclease. In the case of the carboxylated beads of the invention, it is found that the micro-surface of the beads is extremely irregular, presenting an unusually large surface area which may reduce steric hinderance to hybridisation and enzyme activity close to the surface. On the other hand the non-specific binding to such carboxylated beads is not increased.

The superparamagnetic, monodisperse particles carrying oligonucleotides according to the invention may be used in a wide range of procedures. A number of these are set out below.

1. Isolation of mRNA from Mixtures Containing it

The conventional way of obtaining mRNA from an eukaryotic cell extract is taught by T. Maniatis et al (Molecular Cloning: a laboratory manual, pp187–198). Briefly polydeoxythymidine (oligo dT) is bound to agarose beads or cellulose which are used to make an affinity matrix, typically a column. The cell extract is applied to the column and as it passes through the column the polyadenylate tails of the mPA bind to the oligo dT immobilised on the beads. The column is washed and then the mRNA is eluted from the column. This technique is far from ideal, however, not least because of the time it requires, normally at least 2 hours.

All species of RNA are prone to rapid hydrolysis by ribonucleases present in cell lysates so that it is important that mRNA is isolated and reverse transcribed into cDNA as soon as possible after lysis; otherwise a significant fraction of the mRNA could be degraded and full length mRNA corresponding to the DNA of a complete gene would be difficult to locate. Using the conventional way of separating mRNA from a cell extract much time is expended while the mRNA is on the column, leading to unwanted degradation. Furthermore, the column of agarose or cellulose beads becomes contaminated or even clogged with other cell components and cannot be readily reused.

An object of this invention is to provide a rapid method for obtaining and purifying RNA.

According to a further feature of the invention there is provided a method of isolating RNA from a liquid containing it together with other components, which includes the steps of: (a) adding to said liquid a plurality of superparamagnetic monodisperse particles having oligonucleotide probes attached thereto whereby the RNA is hybridised to said probes and thus bound to said particles; (b) magnetically aggregating said particles onto a solid surface; and (c) separating said liquid and other components from said aggregated particles.

To avoid random hybridisation of unwanted RNA and to complete the removal of the remaining components of hybridisation solution, the magnetic particles are preferably washed at least once after the initial magnetic separation. To remove RNA bound by random partial homology, the washing may be carried out under stringent conditions, either by increasing the temperature or by using a lower salt concentration than that used in hybridisation, e.g. 0.5M sodium chloride or an equivalent solution.

Stringency is normally calculated according to the probe length and G:C content. If the homology between the probe oligonucleotide and the target mRNA is inexact, washing should be carried out under less stringent conditions. In general, washing should be carried out at a temperature 12° C. below the melting temperature of the duplex ($T_m$). The approximate $T_m$ may be conveniently calculated according to the following relationships from Maniatis, supra, pages 388–389.

(a) $T_m = 69.3 + 0.41 \cdot (G+C)\% - 650/L$

L equals the average length of the probe in nucleotides.

(b) The $T_m$ duplex DNA decreases by 1° C. with every increase of 1% in the number of mismatched base pairs.

(c) $(T_m)u_2 - (T_m)u_1 = 18.5 \log_{10} \dfrac{u_2}{u_1}$ where $u_1$ and $u_2$ are the ionic strengths of two solutions.

For small oligonucleotides, the melt temperature may be approximated in degrees centigrade as follows:

$T_m = 2 \times (\text{number of } A+T \text{ residues}) + 4 \times (\text{number of } G+C \text{ residues})$ The hybridisation reaction is preferably effected in a 1M sodium chloride solution or an equivalent solution known in the art. (See Nucleic Acid Hybridisation, B D Hames and S J Higgins, IRL Press, 1985).

Removal of the mRNA from the probe may be effected by heat treatment at 65° C. in a suitable buffer, e.g. 1 m EDTA.

The method of the invention can be applied to the separation of all the mRNA material from a cell lysate, for example as a preliminary purification step before isolating a specific mRNA fraction or even a specific mRNA molecule. For this purpose, the probe is advantageously oligo-dT, that is a relatively short chain of deoxythymidine units, e.g. from 12 to 200 bases preferably 15–50 bases. Such a chain may be readily and cheaply prepared by enzymic polymerisation of deoxythymidine or, for the shorter chains, by automated chemical DNA synthesis or traditional polymerisation.

The oligo-dT probes may be directly attached to the beads covalently or by affinity binding. In that case, the hybridised mRNA may subsequently be liberated into solution by heating to give a mixture of purified mRNA at any desired concentration in any desired buffer.

A particular advantage of this embodiment is that if it is attached to the bead via the 5'-terminus, a 3'-terminus of a DNA probe can also serve as a primer for reverse transcription to form single stranded complimentary DNA (sscDNA) which can then, if desired, be used to produce double stranded cDNA, (dscDNA) complimentary to the isolated mRNA in accordance with the International Application of even date herewith corresponding to our United Kingdom Patent Applications 8827158.0 and 8827159.8 the contents of which are incorporated by reference. By attachment of the 5'-terminus of the DNA probe via a linker carrying one or more restriction endonuclease sites, the probe, synthesised dscDNA can be liberated from the beads by restriction enzyme cleavage and the beads separated magnetically.

According to another embodiment of the invention, however, the probes are specific to a target mRNA molecule. The use of specific DNA probes coupled to magnetic particles is of particular value in isolating families of mRNA molecules having a common sequence hybridising to the probe. Thus, for example, the mRNA coding for immunoglobulin may be isolated from a relevant cell extract using DNA probes from the constant regions of the heavy and light chains. In the study of genetically transmitted diseases, it is possible to isolate mRNA transcribed from a series of modified genes using a probe corresponding to a conserved sequence of the gene.

2. Isolation of Single Stranded DNA

The magnetic oligonucleotides according to the invention can be used to isolate ssDNA is substantially the same way as mRNA. Where the DNA is present in a sample in double stranded form as in a cell lysate, a strand separation step is initially required. This is illustrated in the description of polymerase chain reaction described below.

The magnetic particles according to the invention carrying poly dT probes may advantageously be used in isolation of specific target nucleic acid sequences. A probe may be synthesised comprising a DNA sequence complementary to a known sequence of the target nucleic acid and in addition, a poly dA tail, for example of 10–25 dA units. The probe is caused to hybridise to the target nucleic acid and a further labelled probe is caused to hybridise to a different sequence of the nucleic acid. The magnetic particles carrying poly dT may then be used to capture the ternary complex, the capture conditions being such that only hydrogen bonding between the poly dT and the poly dA occurs. The relatively weak poly A/poly dT bonding is readily reversible, e.g. by heating or by washing with guanidine thiocyanate buffer. Thus, after removal of the magnetic particles from the hybridisation solution and washing, the ternary complex may be eluted from the particles and, for further selective purification, subjected to one or more further cycles of capturing. This technique is particularly effective in avoiding contamination of the labelled target nucleic acid with excess label, a common source of "noise" in conventional assay systems.

3. Sequencing of Single Stranded RNA or DNA

There are two major techniques for sequencing DNA; the Maxam-Gilbert method and the Sanger Dideoxy Method. The Maxam-Gilbert method starts with a DNA that is labelled at the 5' end of one strand. The labelled DNA is then preferentially cleaved at one of the four nucleotides. Conditions are chosen so that an average of one break is made per chain. In the reaction mixture for cleavage at a given base each broken chain yields a radioactive fragment extending from the 5'-terminus to one of the positions for that base, and such fragments are produced for every position of the base. The fragments are then separated e.g. by PAGE and an autoradiogram made of the gel. By determining the chain lengths up to each base cleaved one can determine the overall sequence. The Maxam-Gilbert method can be used to determine sequences of more than 250 bases.

The Sanger dideoxy method for DNA sequencing relies on the controlled interruption of enzymic replication. DNA polymerase is used to copy a particular sequence of a single-stranded DNA. The synthesis is primed by a complementary fragment. In addition to the four deoxyribonucleoside triphosphates, the incubation mixture contains a 2',3'-dideoxy analogue of one of them. Either the dideoxy analogue or one of the deoxyribonucleoside triphosphates may be labelled. The incorporation of this analogue blocks further growth of the new chain because it lacks the 3'-hydroxyl terminus needed to form the next phosphodiester bond. Hence, fragments of various lengths are produced in which the dideoxy analogue is at the 3' end. Four such sets of chained-terminated fragments (one for each dideoxy analogue) are then electrophoresed on a gel, and the base sequence of the DNA is read from the autoradiogram of the four lanes. Recently, a variant of the dideoxy method has been devised which involves the attachment of a fluorescent tag to the oligonucleotide primer; a differently coloured one in each of the four chain-terminating reaction mixtures. The reaction mixtures are combined and electrophoresed together. The separated bands of DNA are then detected by their fluorescence as they pass by a detector. Sequences of up to 500 bases can be determined in this way but in general, shorter sequences such as about 250 bases are preferred.

Significantly longer sequences of DNA have to be split into smaller fragments (250–550 bases) before being sequenced by either method. Usually overlapping fragments are necessary so that the sequence data can be assembled correctly. The formation of overlapping fragments creates another step in the determination of a DNA sequence.

One commonly used sequencing system clones the DNA sequence in the M13 phage which provides a single DNA strand. Where the sequence is longer than 500 base pairs the usual technique is to sequence a first section and then, using the information so gained, synthesise a primer for the next section of 500 bases, repeating this procedure until the whole DNA strand is sequenced. However, it is necessary to use a new sample of the cloned M13 phage each time because all the DNA material including the template DNA has to be loaded onto the gel. There is a need for a method of sequencing nucleic acids which avoids the need for forming sub-fragments of large pieces of nucleic acid. Also, there is a need for a method which is simple, rapid and lends itself to automation.

According to a still further aspect the invention provides a method of sequencing single stranded nucleic acids which comprises the steps of:

(a) Preparing superparamagnetic monodisperse particles carrying an oligonucleotide (DNA or RNA) to be sequenced;

(b) either (i) dividing the particles into four aliquots and adding to each aliquot a polymerase, mixed nucleoside triphosphates and a single dideoxynucleoside triphosphate, the latter being different for each aliquot and, if required a primer, at least one of the primer or nucleoside or dideoxynucleoside being labelled; or (ii) adding to all the particles a polymerase, mixed nucleoside triphosphates, four different dideoxy nucleoside triphosphates each carrying a different label and, if required a primer, whereby a series of labelled DNA strands are synthesised each having different chain lengths and ending with a particular dideoxy base, (c) liberating the labelled DNA strands and size fractionating these; and (d) determining the sequence.

It should be noted that the single stranded nucleic acid to be sequenced is an oligonucleotide and that step (a) comprises the formation of magnetic particles with attached oligonucleotides according to the invention. It will be appreciated that where the nucleic acid to be sequenced is DNA, the polymerase may be a DNA polymerase and where it is RNA, the polymerase will be a DNA polymerase or a reverse transcriptase.

To ensure identification of the fragments on size fractionation, the primer sequence may have a label attached thereto or the nucleoside triphosphates or dideoxy-bases may be labelled e.g. by using radioactive phosphorus. It is a feature of the present system of sequencing that excess label may be removed from the system by magnetic separation of the magnetic particles from solution together with both template nucleic acid and cDNA fragments attached thereto and liberation of the cDNA fragments into a sequencing buffer. In prior methods of sequencing, excess label interfered with the image from the sequencing gel.

One particularly effective procedure according to the invention is firstly to clone DNA to be sequenced in a cloning vector to provide a sufficient quantity of the DNA for sequencing. All types of cloning vectors can be used. The DNA may then be excised at suitable RE sites in the vector, conveniently leaving attached sections of the vector (which have already been sequenced) to provide a suitable point of attachment to the magnetic particles.

When the double stranded DNA sequence is attached to the beads via the 3'-biotinylated sequence, it may be denatured to leave a single strand comprising the DNA to be sequenced linked to the magnetic beads via the adjacent primer section.

A primer complementary to the above may be annealed thereto and labelled e.g. by adding a radioactive nucleotide and a polymerase primer section and annealing. Sequencing including size fractionation may then be effected as outlined above. Sequencing will usually be continued only for about 250 bases to permit accurate size fractionation. This can be achieved by adjusting the ratio of dideoxy to normal nucleotides. The cDNA fragments synthesised can be removed by denaturation without damage to the DNA on the beads. The sequence information may then be used to design a short primer for the next series of bases to be sequenced. In this way, a very long DNA strand (e.g. 2000 bases) may be sequenced in sections without encountering the overlapping problems found in the conventional method.

The primer sequence incorporated into the cloning vector is conveniently the so-called "universal primer" used in conventional M13 sequencing. All vectors containing lac Z' gene contain this primer, which has the sequence (SEQ ID NO:1) 5'GTAAACGACGGCCAGT3'.

The sequencing method of the invention may take a number of forms:

A. The DNA strand to be sequenced may be 3' biotinylated and attached to magnetic particles carrying streptavidin. If desired, double stranded DNA may be attached in this way and subsequently denaturated to provide the single strand required for sequencing. It should be noted that this permits the separated strand to be isolated from the supernatant uncontaminated with the immobilised strand and this further strand can be sequenced separately to provide confirmation of sequence information. A primer is hybridised to the 3'-terminal region of the DNA, followed by deoxy and dideoxy bases as above to sequence up to about 500 bases, a further primer being required as described above to sequence the next section.

B. The DNA strand to be sequenced may be hybridised to a linker carried by the magnetic particles, the linker being in the form of a loop of single stranded DNA in which the 5'-end is hybridised to a region near the 3'-end to leave a sticky end corresponding to the 3'-terminal region of the DNA strand. Such a loop may be attached to the magnetic particles via an amino or biotin grouping which can react with carboxyl or streptavidin groups respectively carried by the particles. The DNA strand may be dephosphorylated at the 3'-terminus and then be ligated to the 5'-end of the loop to provide a covalent attachment. Double stranded DNA having a sticky end corresponding to that provided by the loop may be attached in this way and the second strand subsequently removed by denaturation, to leave the 3'-end of the loop as a primer for sequencing the first section of up to 500 bases.

C. The magnetic particles may carry a probe hybridising to a section of DNA, the probe thus serving as a primer for sequencing the first section. The DNA sequence hybridising to the probe is preferably 3'- to the DNA to be sequenced. This is commonly possible where the latter DNA is excised from a vector together with additional terminal DNA sequences. Where the nucleic acid is a mRNA the probe may be a 5'-attached oligo-dT sequence hybridising to the poly A tail of the native eukaryotic mRNA. Alternatively, the probe may be a specific DNA sequence hybridising to a sequence in the mRNA, for example where the 3'- terminal sequence of the mRNA is already known.

Where the sequencing method requires the primer to carry the label, the probe also functioning as a primer should carry appropriate RE sites to allow the synthesised DNA strands to be detached from the particles together with the label. This requirement applies to both of methods 2) and 3). However, it is also possible to simply use a separate labelled primer which is not covalently attached to the probe and thus readily detaches together with the synthesised DNA strands.

4. Amplification of a Target Nucleic Acid by the Polymerase Chain Reaction (PCR)

Target DNA molecules are often present in cell lysates or other source materials in extremely small quantities and in order to amplify such DNA selectively before sequencing, the polymer chain reaction (PCR) method may be used. The PCR method may be used to amplify target DNA rather than using a cloning step. In the PCR technique a pair of polymerisation primers specific to known sequences of the target DNA are selected, one hybridising at or near the 5' end of the coding strand and the other at or near the 5' end of the non-coding strand such that in the presence of a polymerase, each primer produces a DNA sequence extending the full length of the target DNA template. If the DNA so produced is then subjected to strand separation, typically by melting at a temperature of about 90° C., the newly formed single stranded DNA sequences will hybridise to excess primer present in the mixture, usually after reducing the temperature to the range suitable for annealing, whereupon in the presence of the polymerase, further DNA strands are synthesised, this time extending only between the termini of the two primers. The polymerase is preferably capable of surviving the high temperature used in the strand separation step, a suitable thermophilic polymerase, namely Taq I, having recently become available. If an excess of the two primers and of nucleotides needed for DNA synthesis is maintained in the medium, it is possible to operate a repeated cyclic process in which the separate strands are synthesised, separated, annealed to primer and new strands synthesised, merely by raising and lowering the temperature between the optimal temperatures for each of the above stages. In this way, it is found that amplification of the original target DNA can be exponential and million-fold increases of concentration can be effected in a relatively short time.

However, this procedure is not always sufficiently selective due to a percentage of non-specific binding of the primers to other DNA sequences, thereby amplifying the latter in addition to the target DNA. This amplification of random portions of sample DNA, due to the non-specific binding of the primers, leads to an increase in background noise relative to the signal from the target DNA. In many cases this increase in the level of background noise can severely affect the usefulness of this technique.

In relation to molecular cloning, it has been suggested that this problem of non-specific binding of the primers may be overcome by using a second pair of primers nested within the first. By requiring four separate priming events to take place considerable reduction in non-specific amplification is achieved (see Mullis, K. B. K Faloona, F. A., Methods in Enzymology (1987) 155 pp 335–350, and Wrischnik, L. A. et al. Nuc. Acids Res. (1987) 15 pp 529–542). Engelke, D. R. et al (Proc. Natl. Acad. Sci USA (1988) 85 pp 544–548) suggests that only one new primer, nested inside one or other of the original primers, can lead to a larger and more consistent amplification of the target DNA.

We have found that magnetic beads with attached oligonucleotides according to the invention can be used as one of the primers in a PCR amplification procedure. The kinetics of the reaction are close to those found in solution. Where a second pair of nested primers is used, the particles according to the invention need only be used in the second PCR phase. In each case, all the amplified DNA is immobilised on magnetic particles and can readily be washed to remove excess reagents. It is preferred to provide an RE site or other reversible bond between the particles and the oligonucleotide probe/primer so that the amplified DNA can eventually be removed.

It is also possible to carry out PCR using a biotinylated probe/primer and to use magnetic particles according to the invention coated with avidin or streptavidin to isolate the amplified DNA.

5. Labelling of a Target Nucleic Acid and Assay Thereof

Our International Patent Application of even date herewith corresponding to United Kingdom Patent Application No. 8827160.6 the contents of which are hereby incorporated by reference, describes a method of labelling a target nucleic acid wherein magnetic particles carrying an oligonucleotide probe specific to a known sequence of the target nucleic acid is added to a mixture containing the latter and using the probe as a primer together with a polymerase and suitable bases, a cDNA strand is synthesised incorporating a number of labelled nucleotide bases. This procedure is particularly simple and rapid and may be used to assay the target nucleic acid quantitatively or qualitatively.

6. Synthesis of cDNA

Our International Patent Application of even date herewith corresponding to United Kingdom Patent Applications Nos. 8827158.0 and 8827159.8, the contents of which are hereby incorporated by reference, describes the synthesis of cDNA by hybridising magnetic particles carrying oligonucleotide probes to a target nucleic acid and using the probe as a primer, together with a polymerase and nucleotide base, a cDNA strand is synthesised. This method may be used to synthesise individual cDNA molecules or to prepare cDNA corresponding to all of a particular type of nucleic acid present, for example all in RNA.

7. Kits for Procedures Using Magnetic Particles According to the Invention

The invention further provides kits for carrying out the processes of the invention.

A. Kit for Isolation of all mRNA in Sample (a) Magnetic particles according to the invention carrying oligo-dT and one or more of
(b) Hybridising buffer
(c) Washing buffer.

B. Kit for Isolation of Specific mRNA or ssDNA From Sample (a) Magnetic particles according to the invention carrying a specific oligonucleotide and one or more of:
(b) Hybridising buffer
(c) Washing buffer.

C. Kit for DNA or RNA Sequencing (a) Magnetic particles according to the invention carrying oligo-dT or a specific oligonucleotide
(b) A polymerase and one or more of:
(c) Appropriate buffers
(d) Dideoxynucleotides ddT, ddA, ddC and ddG
(e) Deoxynucleotides dT, dA, dC and dG
(f) Dideoxynucleotides, deoxynucleotides or an oligonucleotide, each carrying, or adapted to carry, a label.

D. Kit for Polymerase Chain Reaction (PCR)

(a) Magnetic beads according to the invention carrying a standard specific DNA probe/primer for the 3'-end of the target nucleic acid;
(b) a standard PCR 5'-primer, optionally labelled;
(c) a thermostable polymerase; and one or more of
(d) appropriate buffers; and
(e) a restriction endonuclease.

The following Examples are given by way of illustration only:

EXAMPLE 1(a)

Carbodiimide (EDC) Mediated Attachment of 5'-NH$_2$ Probes to Carboxyl Beads (a) The reaction used for attaching probes to carboxyl beads is as follows. Amino groups introduced at the 5'-end of the probes using a one-step reaction method described by Chu et al. (Chu, B. C. F., and Orgel, L. E. (1985) DNA 4, 327–331.), results in a greater nucleophilicity of the terminal primary amino group of the alkyl linker as compared to the amino functionalities of the bases. It was therefore expected that the carboxyl groups on the beads would react preferentially with these primary amino groups.

100 ug 5'-NH$_2$ modified probe in 600 ul of 0.1M imidazole-buffer pH 7, 0.1M EDC were added per mg of R452 carboxyl beads. The reaction mixtures were incubated for 20 hours at room temperature with gentle shaking.

(b) NH$_2$ modified probes were made using Applied Biosystem synthesizer and AMINOLINK II.

The coupling reactions were as follows:

10 μg 5'NH$_2$ modified probe in 100 μl of 0.1M imidazole buffer pH 7.0, 0.1M EDC was added per mg of R452 carboxyl beads. The reaction mixtures were incubated for 20 hours at room temperature on a roller mixer (Coulter) followed by washing in TE buffer containing 0.1M NaCl (4x).

Hydridization efficiency:

A range of beads with different amount of probe attached were tested in hybridization experiments with a complementary 25 mer polydT probe.

The beads covered the range 1–250 pmol probe attached per mg beads.

Increasing amounts of 25 mer polydA oligonucleotide hybridized with increasing amounts of probe attached. 193 pmol hybridized to beads with 250 pmol attached. However, when the target molecule was in the range of 1000 bp (control mRNA Promega Corporation) there was no difference in hybridization efficiency between the bead with 100 pmol of attached probe compared with the more densely coupled beads.

EXAMPLE 2

Carbodiimide (EDC) Mediated Attachment of 5'-Phosphate-Probes to Amino Beads

Probes were attached via a phosphoramidate linkage to 3 different amino beads by the method described by Ghosh et al. (Ghosh, S. S., and Musso, G. F. (1987) Nucl. Acids Res. 15, 5353–5372.). The amount of DNA attached to the different beads varied from 1.4–11.3 micrograms/mg.

The R469 beads which carry an amino group at the termini of an polyethylene glycol linker (8 atoms), bind a larger amount of probes than R240 beads which carry the amino group on a shorter linker (3 atoms). When the linker is made longer (number of atoms 20) as in the case of for the R442 beads, a decrease in the amount of probes bound to the beads is observed. This is probably due to secondary structures of the linkers which results in the terminal amino group becoming unavailable for coupling.

The amount of non-specifically bound DNA varies amoung the beads (7–30%) probably according to number of amino groups per unit of surface area. The R469 beads, which bind the largest amount of probes covalently (11 ug/mg), showed the lowest non-specific binding.

The acid lability of the phosphoramidate bond (Chu, B. C. F., Wahl, G. M., and Orgel, L. E. (1983) Nucl. Acids Res. 11, 6513–6529.) is used for measuring degree of end-attachment by acid hydrolysis. The amount end-attached probes varies between the different beads from 20–65%, and again, the R469 bead seems to be the preferable one with 65% of the probes end-attached.

We were able to attach twice as much probe material to the R469 beads by performing the reaction in imidazole buffer pH 7 for 3 hours at 50° C., instead of pH 6, for 24 hours at room temperature. An increase in molarity of EDC from 0.1M to 0.2M resulted in a 20% decrease in amount of probes on the R469 beads (data not shown).

General Method 600 pmole (6 ug) of oligo A (36 mer) were dissolved in 1 ml of 0.1M imidazole, pH 7, 0.1M EDC and mixed with 5 mg of amino beads, and incubated for 3 hours at 50° C.

EXAMPLE 3

Coupling of 5'NH$_2$ Probes to Tosyl Activated Beads

NH$_2$ groups were introduced at the 5' end of oligonucleotides using Applied Biosystems DNA Synthesizer 381A and AMINOLINK II to introduce the primary NH$_2$ group at the 5' end. AMINOLINK II is supplied from Applied Biosystems. After synthesis these amino modified oligonucleotides were used directly in the coupling experiment.

Tosyl activated M-280 beads are commercially available from DYNAL AS, Oslo.

Coupling procedure:

10 mg of tosyl activated beads were mixed with 50 μg NH$_2$ modified oligonucleotide in 100 μl 0.5M Na$_2$HPO$_4$ and incubated at 37° C. for 20 hours on a roller mixer (Coulter) followed by washing in TE buffer containing 0.1M NaCl (4x).

EXAMPLE 4

Direct Synthesis

DYNABEADS R 488 beads were used. They are the same beads as M-280 except that the diameter is 3.15 microns instead of 2.8 microns and they contain primary OH groups on the surface as in the M-280 beads.

Using the synthesizer (Pharmacia GENE ASSEMBLER) the 3' end of DNA will be attached to the surface.

Only small modifications were necessary to fit the 3.15 micron beads. In the standard small scale column from Applied Biosystems teflon filters with cut off at 3.0 microns were installed, the beads loaded and the column assembled.

Since this support does not contain dimethyltrityl (DMTr) groups and this machine stops if no such chemical is released in the first steps in the first cycle, small modifications in the start procedure were introduced. The synthesis was started using a standard ABI small scale column until the DMTr groups were released. Then the Gene Assembler was stopped manually and the modified column with magnetic beads was put into the Gene Assembler. The standard synthesis programme as recommended by the manufacturer was then followed. Deprotection was as recommended by Pharmacia. Direct synthesis was used to produce oligo(dT)$_{25}$ and the following sequence (SEQ ID NO: 2) from the C region of the kappa light chain gene:

5'-TCACTGGATGGTGGGAAGATGGATA-CAGTTGGTGCA-3'.

EXAMPLE 5

Materials and Methods Magnetic Beads

DYNABEADS M-280 STREPTAVIDIN (Dynal A. S, Box 158, N-0212 Oslo) were used as solid phase. These are monodisperse superparamagnetic polymer particles with a diameter of 2.8 μm covalently coupled with Streptavidin.

They have a surface area of 4.3 m²/g.

Biotin Binding Capacity

100 µl 6×SSPE (Standard saline with phosphate and EDTA: Maniatis) containing 1 nmol $^{14}$C-Biotin (Amersham) was added to 0.5 mg beads (prewashed in 6×SSPE) and placed on a roller mixer (Coulter) at room temperature for 15 minutes.

After two separate washes in 6×SSPE the fraction of bound $^{14}$C-Biotin was measured by scintillation counting.

Deoxyoligonucleotides

Deoxyoligonucleotides were synthesized on an Applied Biosystems 381A DNA synthesizer.

Chemicals were purchased from Applied Biosystems. 5'amino modified deoxyoligonucleotides were made using AMINOLINK II.

The immunoglobulin light kappa chain probe used was (SEQ ID NO: 2):

5'-TCACTGGATGGTGGGAAGATGGATA-CAGTTGGTGCA-3'.

Biotinylation of Probes

Biotin XNHS ester (Clontec N-succinimidyl of N-biotinyl ε-caproic acid) was used as recommended by the supplier.

0.1 µmol of $NH_2$-modified oligo(dT)$_{25}$ in 90 µl of water was added 10 µl labelling buffer (1M sodium bicarbonate/carbonate, pH 9.0) and vortexed.

Finally 25 µl Biotin XNHS ester (100 mg/ml) in dimethylformamide was added and incubated at room temperature overnight.

Excess labelling reagent and buffer was removed in a Sephadex G50 spin column.

The 5'Biotin oligo(dT)$_{25}$ was endlabelled using the fill in reaction by Klenow polymerase, α-[$^{32}$P]-dTTP and oligo(dA)$_{25}$ as template. Excess label was removed using a Sephadex G50 spin column.

Preparation of Oligo(dT) Dynabeads (T-beads)

200 µg Biotinylated oligo(dT)$_{25}$ (24 n mol) in 2.5 ml 6×SSPE was mixed with 50 mg prewashed DYNABEADS M-280 Streptavidin and incubated on a roller mixer for 15 minutes at room temperature.

After two washes in 6×SSPE the beads were stored at 4° C. in 6×TE, 0.1% SDS.

Oligonucleotide Hybridization Assay

In the standard assay to measure hybridization capacity of different batches of T-beads, 0.1 mg of the beads in an eppendorf tube was washed once with 6×SSPE, 0.1% SDS. A magnet rack (MPC-E, Dynal A. S., Oslo) was used to aggregate beads between each step.

After removal of the washing buffer, 50 µl hybridization solution (6×SSPE, 0.1% SDS), containing 50 pmol of oligo(dA)$_{25}$ with trace amount (1-2×10$^5$ cpm) α-[$^{32}$P]-dATP-labelled oligo(dA)$_{25}$ was added.

After gentle mixing the tube was left to hybridize for two minutes at room temperature.

The hybridized beads were washed twice with 2× SSPE, 0.1% SDS at room temperature and the percentage of oligo(dA)$_{25}$ hybridized to the oligo(dT)$_{25}$ Dynabeads was measured in a scintillation counter.

Labelling of Poly A mRNA Tracer

1 µg 1200 bp mRNA with a 3'polyA$_{30}$ tail (Promega) was mixed with 2.5 pmol oligo(dT)$_{25}$ in 10 µl 5×Klenow buffer, 1 u RNasin (Promega), 10 mM DDT. After two minutes at room temperature 10 µCi α-[$^{32}$P]-dATP, 1 u Klenow polymerase (Amersham) and water up to 50 µl were added and incubation continued for 60 minutes at 15° C. Excess α-[$^{32}$P]-dATP was removed using a Sephadex spin column.

Buffers for Poly(A) mRNA Hybridization to DYNABEADS M-280 STREPTAVIDIN Coupled with Oligo(dT)$_{25}$ Poly(A) binding buffer:
0.5M LiCl, 10 mM Tris-Cl, pH 7.5, 1 mM EDTA, 0.1% sodium dodecylsulphate.

Middle wash buffer:
0.15M LiCl, 10 mM Tris-Cl, pH 7.5, 1 mM EDTA, 0.1% sodium dodecylsulphate.

Elution buffer: 2 mM EDTA, 0.1% SDS. Depending on the subsequent use of the purified mRNA SDS may be omitted in the last washing step and in the elution buffer.

Extraction of Total RNA

Extraction of total RNA from cell cultures was carried out using the sarcocyl-, LiCi-, Urea-method according to the protocol of Auffrey and Rougeon (1980, Eur. J. Biochem, 107, 303–314).

DNA Coupling and Hybridization Capacity

The DYNABEADS M-280-STREPTAVIDIN used in the present experiments were found to bind 390 pmol $^{14}$C-Biotin pr. mg of beads.

The amount of coupled 5'Biotinylated oligo(dT)$_{25}$ was determined using a labelled tracer in the coupling reaction and found to be 250 pmol Biotin oligo(dT)$_{25}$ per mg of beads.

To determine the maximum hybridization capacity of these magnetic oligo(dT)$_{25}$ beads a standard assay was designed using a (dA)$_{25}$ oligonucleotide as described in materials and methods.

The batch of T-beads made and used in the present study were found to have a hybridization capacity of 193 pmol oligo(dA)$_{25}$/mg.

In a control experiment to measure unspecific binding, beads coupled with a non-complementary probe (a 42 mer Tn917 probe) bound less than ten attomol of oligo(dA)$_{25}$/mg beads.

Hybridization Kinetics with Oligonucleotides

Before starting the magnetic mRNA isolation experiments it was necessary to study the hybridization kinetics of the system.

Hybridization experiments were set up using less than two fold excess of T-bead hybridization capacity to the complementary oligo(dA)$_{25}$ target nucleotide.

Figure 1:
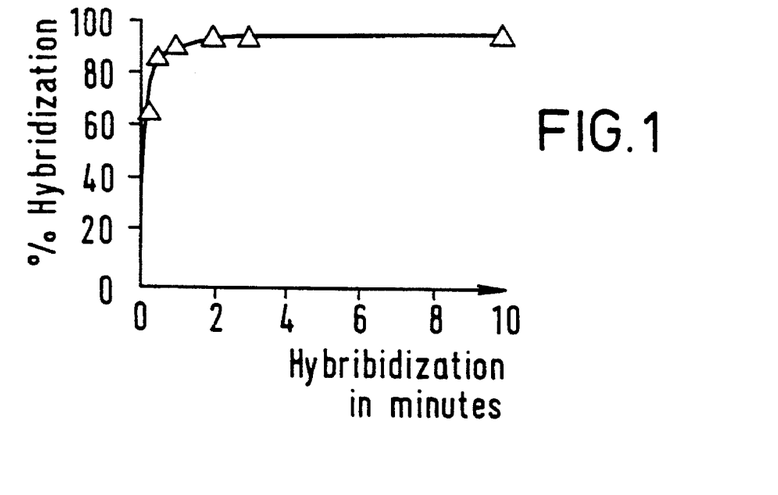
FIG. 1 is a graph showing that hybridization of T-beads to oligo(Da)$_{25}$ was essentially complete in less than one minute, as described in Example 5.

As FIG. 1 shows, hybridization was complete within one minute.

Hybridization Efficiency with Oligonucleotides

To test how efficiently target nucleic acids can be separated from a mixture, we set up two different experiments.

Figure 2A:
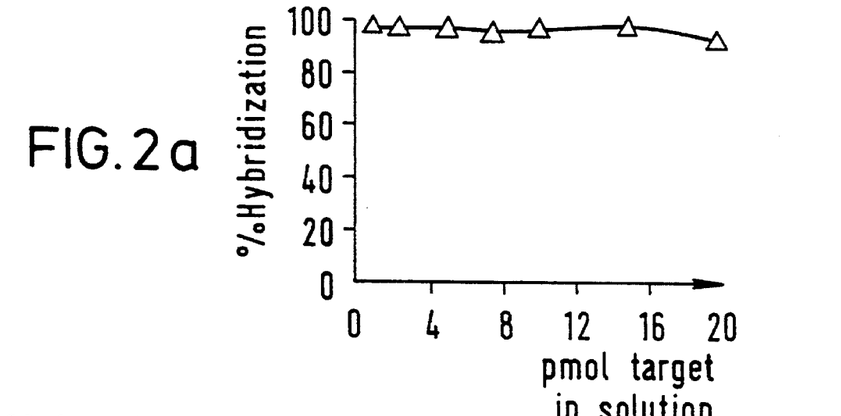
FIG. 2A is a graph showing that T-beads bind at least 99% of oligo(Da)$_{25}$ even when the molar ratio of target nucleic acid to bead capacity is nearly 1:1, as described in Example 5.

In the first experiment increasing amounts of target oligonucleotides (oligo(dA)$_{25}$) were added to a fixed amount of T-beads (100 μg) with a known maximum hybridization capacity of 19 pmol. The results in FIG. 2A demonstrate that the T-beads are able to bind at least 99% of the target oligonucleotides even when the molar ratio of target to bead capacity is aproaching 1:1.

Figure 2B:
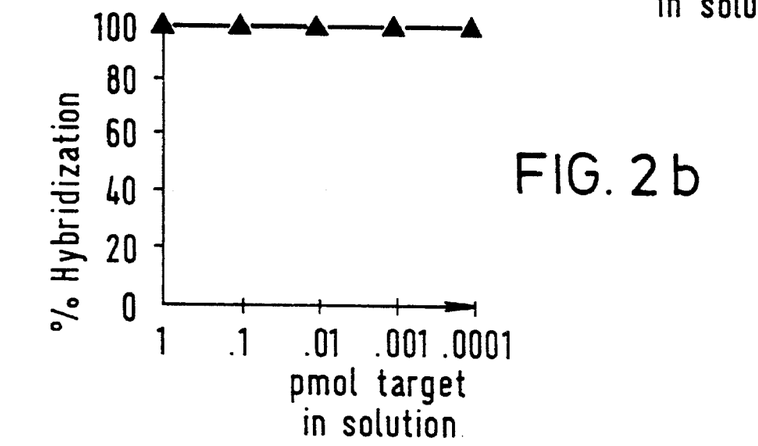
FIG. 2B is a graph showing that T-beads recover more than 95% of an oligo(Da)$_{25}$ target nucleic acid in a sample at very low levels, as described in Example 5.

In the second experiment, five different concentrations of oligo(dA)$_{25}$ from 1 pmol down to 100 amol were added to 100 μg aliquots of beads. The total amount of nucleic acids present in each mixture was adjusted up to 10 pmol with a probe comprising an irrelevant oligonucleotide. In a negative control experiment without target oligonucleotides the noncomplementary probe was labeled to be able to detect nonspecific binding. After hybridization for two minutes followed by two washing steps the amount of oligo(dA)$_{25}$ hybridized was measured. The results in FIG. 2B show that even at a target oligonucleotide amount as low as 100 amol (0.001% of total nucleic acids present) the magnetic oligo(dT)$_{25}$ beads take out more than 95%.

Magnetic Isolation of PolyA mRNA

The capacity, efficiency and kinetics of (dT)$_{25}$-DYNABEADS binding polyA mRNA was studied by setting up a similar set of experiments as described for oligonucleotide hybridization.

To determine the maximum polyA mRNA binding capacity of the T-beads we used a $^{32}$P-labelled control RNA of known concentration which was a 1200 nucleotide kanamycin transcript having 30 A's at the 3' end (Promega). The strategy for determining the binding capacity was as described for oligonucleotide binding assay, but using the hybridisation buffers set out above.

The binding capacity of this particular polyA$_{30}$ mRNA was found to be 33 pmol (13 μg) mRNA per mg T-beads.

Kinetics and Efficiency of PolyA mRNA Hybridization to T-Beads

Figure 3:
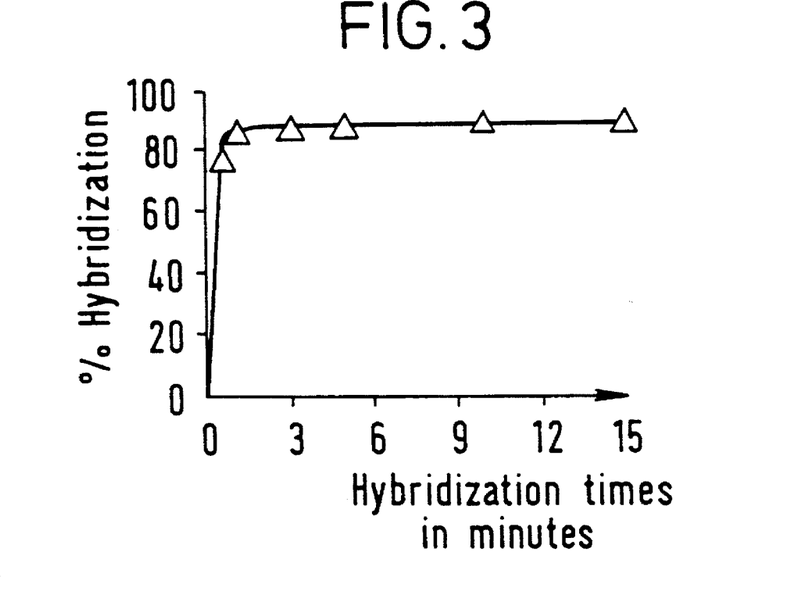
FIG. 3 is a graph showing that hybridization of polyA mRNA to T-beads is 90% complete in less than two minutes, as described in Example 5.

Total RNA was extracted from 1×10$^8$ cells of the hybridoma cell line AB1 (11) using the above method of Auffray et al. The kinetics of mRNA hybridization to the oligo(dT) beads were determined using 10 μg total RNA together with trace amount of $^{32}$P-labelled mouse pancreas polyA mRNA (Clontec), and approximately five fold excess T-bead capacity in 150 μl hybridization buffer. The results in FIG. 3 show that close to 90% of the polyA mRNA in the sample was hybridized to the beads in less than two minutes and as much as 78% already after 30 seconds.

Direct Magnetic Isolation of PolyA mRNA from Cell Cytoplasm

Figure 4:
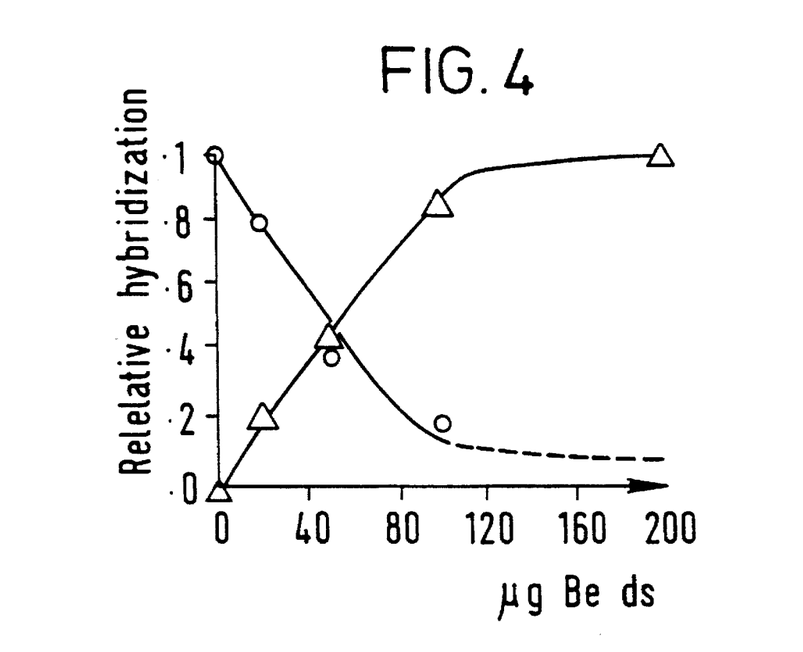
FIG. 4 is a graph showing that more than 90% of cytoplasmic polyA MRNA from $10^6$ cells can be recovered on about 120 μg of T-beads, as described in Example 5. Triangles denote hybridization of MRNA to the T-beads and circles denote MRNA remaining in the supernatant.

10$^6$ cells from a culture of the hybridoma cell line AB1 were washed once and resuspended in 50 μl PBS (Dulbecco, 041-04190) and Triton X-100 was added to a final concentration of 0.5%. After lysis for 1 minute the cell debris, including nucleine, was pelleted by a 10 second spin in an Eppendorp centrifuge. The supernatant was added to T-beads in 100 hybridization buffer of double concentration and left to hybridize for 2 minutes followed by magnetic aggregation of the beads. The hybridized mRNA was detached from the beads in 2 mM EDTA at 65° C. and beads were removed using the magnet. In this experiment aliquots of 10$^6$ hybridoma cells were added to varying amounts of T-beads, 200 μg, 100 μg, 50 μg, 20 μg and 200 μg of DYNABEADS M280-STREPTAVIDIN without probe. Densitometric scansof the X-ray films from Northern blots of poly mRNA after detachment from the T-beads and probing with a immunoglobuline kappa light chain probe. These results indicated that the yield of mRNA increases with increased amounts of beads, while the remaining mRNA in the supernatant is correspondingly reduced. The results presented in FIG. 4 show that approximately 120 μg of T-beads is sufficient to isolate more than 90% of cytoplasmic polyA mRNA from 10$^6$ cells. The symbol —Δ— in the figure represents hybridization to beads and the symbol —o— represents mRNA remaining in the supernatant). Streptavidin beads without probe gave no detactable mRNA binding.

EXAMPLE 6

Purification of mRNA from the Eucaryotic B-cell Line "Raji" (Supplied by Dr G Klein, Stockholm, Sweden)

Total RNA was extracted from 1.10$^8$ cells by the method described by Auffray et al., Eur. J. Biochem. 107, 303–314 (1980). According to this method a 0.5 ml cell pellet was added to 5 ml ice cold lysis buffer (3M LiCl, 6M Urea, 0.1% sarkosyl, 0.1M 2- mercaptoethanol, 50M Tris-HCl, pH 7.4, 5 mM EDTA). The mixture was then sonicated and kept on ice overnight.

Next day the lysate was centrifuged at 17.000 g for 20 minutes. The pellet was quickly dissolved in TE-SDS (10 mM NaCl 1 mM EDTA, 0.5% SDS) and extracted once with an equal volume of phenol-chloroform (1:1), then once more with only chloroform. The lysate was mixed with 3 volumes ethanol and $\frac{1}{10}$ volume 3M NaAc, mixed and divided into 10 batches and stored at −20° C. until use.

One batch of total RNA corresponding to 1.10$^7$ cells were subjected to conventional mRNA purification using oligo dT-cellulose (Pharmacia) according the method described by Maniatis, 1982, pages 197–198.

Another batch of total RNA was used in the mRNA purification method as follows:

A DNA probe named RET with a structure (the DNA bases of which are set forth in SEQ ID NO:9)

5'(NH$_2$) (CH$_2$)$_{12}$-GACCTTGGGAATTCCCCGGGCTG-CAGT-(T)$_{24}$ made by a DNA synthesis machine (Applied Biosystems) was coupled to magnetic beads R502 by the carbodiimide method (described previously) by mixing 20 mg of beads, 50 ug of the DNA probe, 48 mg EDC (sigma) in 2.5 ml 0.1M imidazol buffer pH 7.0. Incubation overnight and washing beads twice in TE (above) and once in 0.2M NaOH, 0.5M NaCl gave beads with a capacity to hybridize 8 pmols of an oligoA$_{17}$ probe. The hybridisation capacity was measured by incubating 0.5 mg of the beads with 100 pmols A$_{17}$ probe (labelled with $^{32}$P by kinase reaction) in 6×SSPE for 10 minutes. After washing the beads twice with 6×SSPE at 22° C. (12 degrees below the melting temperature) the fraction of hybridized A$_{17}$ compared to the total amount added was measured in a scintillation counter.

As a negative control in the mRNA purification an irrelevant probe named Tn having the sequence (the DNA bases of which are set forth in SEQ ID NO:10)

NH$_2$—(CH$_2$)$_{12}$—5'NH$_2$—(CH$_{12}$)—TTAATTATCAGT-TAAAGCTTCCTGTT—    GCACTTTTGGGGTGAAG-GAAAAACC—3' was coupled to beads by the process described above.

A Raji mRNA tracer was prepared by radioactive labelling with 0.1 ug and mRNA purified by the conventional method as mentioned above. The labelling was done by hybridising 1 pmol of the RET-probe to the mRNA in 10 ul 5×klenow polymerase buffer (0.25M Nacl, 0.25M Tn$_4$HCl, pH 7.5, 5 mM EDTA) at 15° C. for 10 minutes. 10u Ci α-[$^{32}$P]dATP (Amersham), 2 units of klenow polymerase (BRL) were then added to the mixture, which was diluted to 50 ul with water. After incubation for 2 hours the mixture was passed through a SEPHADEX G50 (Pharmacia) spin column to remove unincorporated nucleotides.

The mRNA purification experiment was then set up as follows:

1 mg of beads with RET probe was added to 20 ug of total RNA from B-cell line Raji, together with 100,000 cpm of Tracer mRNA in 100 ul 6×SSPE.

An identical experiment was set up, but with beads carrying the Tn-probe.

The hybridisation was carried out on a roller machine at room temperature. The hybridisation reaction was followed at short intervals by aggregating the beads by a magnet and measuring the remaining radioactivity in the supernatant. After each measurement the beads were immediately resuspended.

After 10 minutes 60% of the mRNA was bound to the beads with the RET probe. The control beads had not bound detectable amounts of mRNA.

After 30 minutes incubation the beads were washed twice in 500 ul 2×SSC at room temperature, resuspended in 100 ul TE-buffer, heated at 95° C. for 5 minutes, beads aggregated and supernatant collected and stored at— 70° C. use.

EXAMPLE 7

This method has been used to sequence the 5' end of ricin A gene cloned in our laboratory.

Ricin A on a BamHI fragment was cloned in puc 8. The 3' end of the gene was sequenced previously Plasmid pAL400 was cut with SalI and E.coRI and biotinylated using Klenow polymerase with Biotin-dUTP as the only nucleotide present (see Maniatis pp (113–1116). Biotin will only be incorporated in the SalI site. The first primer was based on known sequence data and was (SEQ ID NO: 3) 5'—TGA—ATT—GGA—CT—GCA—AAG—3'

To get rid of unincorporated bio-dUPT, the material was purified using a SEPHADEX G-50 spin column, Maniatis p 466, followed by ethanol precipitation (the ethanol precipitation may perhaps be omitted). The mixture containing biotinylated double stranded DNA was mixed with Streptavidin/Avidin coated magnetic beads in TE buffer (10 mM tris HCl and 1 mEDTA, pH 8.0) by gentle invertion for 30 minutes at room temperature. 2 ug of Biotinylated DNA was used per 10 ul Beads (25 mg beads/ml).

The bound biotinylated double stranded DNA was denaturated in 0.15M NaOH for 5 minutes at room temperature. Beads with single stranded DNA were collected by use of a magnet and washed once in the TE-buffer.

SEQUENCING REACTIONS

Annealing of Sequencing Primer

A mixture containing:
2 ul of 10×reaction/hydridization (100 mM tris pH 8.0, 50 mM MgCl MgCl$_2$)
1 ul of 17 mer primer (1,2 ug/ml)
7.0 ul distilled water
was added to the beads and incubated at 55° C. for 5 minutes and then allowed to cool slowly to room temperature.

To the annealed bead template—primer the following was added:

| [a$^{35}$S] | dATPaS | 1.5 ul (sp.act. 600 Ci/m mol) |
|---|---|---|
| | Klenow | 1.0 ul (4 U/ul) |
| | BSA | 1.0 ul (100 ul (100 ug/ml) |
| | | $^{32}$p may alternatively be used. |

The total mixture is divided into 4 microcentrifuge tubes or wells in a microtiter plate labelled A, G, C and T, i.e. approximately 4 ul in each (because of bead volume).

4 ul of the appropriate nucleotide was added to each tube/well mix viz; A mix, G mix, C mix and T mix.

A mix: 100 uM dGTP, dTTP, dCTP and 100 uM ddATP

G mix: 5 uM dGTP; 100 uM dTTP, dCTP and 12 uM ddGTP

C mix: 100 um dGTP, dTTP; 10 uM dCTP and 100 uM ddCTP

T mix: 100 uM, dGTP, 5uM dTTP, 100 uM dCTP and 500 uM ddTTP

The mixtures were left to incubate for 15 minutes at room temperature.

Complete synthesis of any strands not terminated by a dideoxy nucleotide was effected by adding 2 ul of deoxy nucleotide solution containing 125 of uM of each nucleotide, pH 7.5, and incubated for another 15 minutes.

The reaction was terminated by adding 5 ul of formamide dye and heated in boiling water for 3 minutes in order to denaturate the labelled DNA from the beads. Then, following magnetic separation of the beads template, 3 ul of supernatant containing the labelled DNA was loaded on a buffer gradient sequencing gel: Protocol from Amersham.

The beads with template are reusable after washing and ready for a new primer based on sequencing results from earlier sequencing.

The first primer was based on already known sequence data namely (SEQ ID NO: 3), 5'—TGA—ATT—GGA—CT—GCA—AAG—3'

The two next primers were based on following sequence data from this experiment:

Primer 2 (SEQ ID NO: 4) 5'—G—AGA—TAG—CCT—CCT—CTA—G—3'

Primer 3 (SEQ ID NO: 5) 5'—GCT—CTG—CAT—GAT—TTG—AG—3'

By using these 3 primers it was possible to sequence the first 750 bases in ricin A gene.

As a control the same gene was sequenced using M13. It gave the same result.

EXAMPLE 8

Solid-Phase DNA Sequencing Using PCR Amplified Templates

Solid-phase sequencing using the technique outlined above was performed except that the target sequence was amplified by the PCR technique before immobilization by biotin to streptavidin on the magnetic beads. Plasmid pRIT27 containing a synthetic human proinuslin gene fragment was transformed in to E.coli strain RR1 M15 and plated on agar medium. A single colony was picked up with a sterilised Pasteur pipette and suspended in 10 ul PCR buffer, consisting of 67 mM Tris-HCl, pH 10.00, 16.6 mM (NH$_4$SO$_4$, 6.7 mM MgCl$_2$, 10 mM β-mercaptoethanol and 170 ug/ml BSA. The sample was heated to 95° C. for 5 min and, after cooling to room temperature, neutralized by the addition of 1 ul of a 10×PCR buffer, pH 7.0.

The PCR was performed with two oligonucleotide primers complimentary to a region upstream (SEQ ID NO: 6: biotin—CCATGATTACGAATTTAATAC—3') and downstream (SEQ ID NO: 7: 5'— TTCGATATCGGTAACCAG-CACTCCATGTCATGG—3'), respectively, of the multi-linker region. The upstream primer was biotinylated in the 5'-end as described by the manufacturers (Pharmacia, Sweden).

The reaction mixture (100 ul) consisted of the above described PCR buffer, pH 8.8, 1 uM each of the primers, 200 uM each of dATP, dCTP, and dTTP and the above described 10 ul of lysed sample. Two units of TaqI-polymerase (Amersham, England) was added and temperature cycle reactions were carried out using a Techne programmable DRI-BLOCK PHC-1 (Techne, UK). Each cycle included a heat denaturation step of 92° C. for 1 min, followed by annealing of primers to the DNA for 2 min at 50° C., and DNA chain extension with TaqI-polymerase for 1 min at 72° C. The reaction mixture was covered with a drop of paraffin oil. After 20 cycles, the mixture was added to 100 ul of streptavidin coated magnetic beads. The supernatant was removed and the immobilized double stranded DNA was converted into single stranded form by incubation at 37° C. with 0.15M NaOH for 15 min. The avidin coated beads, with immobilized template DNA was subsequently washed with 0.15M NaOH and TE-buffer.

Sequencing reactions were performed using a fluorescent end-labelled sequencing primer (5'-CGTTGTAAAACGGC-CAGT- 3'), complimentary to a region immediately downstream from the multi-linker region. 2 pmole of the sequencing primer were mixed with the bead immobilized template DNA in a buffer containing 10 mM Tris-HCl (pH 7.5) 10 mM $MgCl_2$, 200 ug ml BSA and 100 mM NaCl to a total volume of 10 ul. The annealing mixture was heated at 65° C. and allowed to cool to room temperature. 1 ul DTT/NaCl mixture (0.8M NaCl/0.1M DTT) and 4 units of T7-polymerase (Pharmacia, Sweden) were added and the volume was adjusted to 15 ul. Then 3.5 ul of aliquots of the mixture were mixed with 2.5 ul of respective nucleotide mixture and incubated 10 min at 37° C. The following nucleotide mixtures were used; 80 uM each dATP, dCTP, dGTP, dTTP, 6.3 uM of respective ddNTP, 50 mM NaCl and 40 mM Tris-HCl pH 7.5. When the extension reactions were complete the supernatants of each reactions were removed and the streptavidin agarose was washed with water. The newly synthesized oligonucleotides were eluted using 3 ul of a formamide/sequencing dye mixture consisting of deionized formamide containing 10 mM EDTA, pH 7.5 0.3% (w/v) xylen cyanol FF and 0.3% (w/v) Bromphenol Blue. After 15 min incubation at 37° C. the supernatant was removed and diluted with 3 ul water. Approx 2 ul were loaded into an automated sequencing apparatus set-up to detect fluorescent bands during electrophoresis (12). A sequencing run with a 20 cm separating length, and 7% polyacrylamide gel, gave clear results. This example illustrates that PCR amplified DNA can be immobilised on magnetic beads and sequenced using T4 DNA polymerase and a fluorescent primer.

---

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:1:

GTAAACGACG GCAGT        15

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:2:

TCACTGGATG GTGGGAAGAT GGATACAGTT GGTGCA        36

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:3:

TGAATTGGAC TGCAAAG                                    17

( 2 ) INFORMATION FOR SEQ ID NO:4:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:4:

GAGATAGCCT CCTCTAG                                    17

( 2 ) INFORMATION FOR SEQ ID NO:5:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:5:

GCTCTGCATG ATTTGAG                                    17

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:6:

CCATGATTAC GAATTTAATA C                                21

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear     ( i i ) MOLECULE TYPE: Other nucleic acid;
        ( A ) DESCRIPTION: Synthetic DNA oligonucleotide     ( x i ) SEQUENCE DESCRIPTION: SEQ ID NO:7:

TTCGATATCG GTAACCAGCA CTCCATGTCA TGG                    33

( 2 ) INFORMATION FOR SEQ ID NO:8:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( x i ) SEQUENCE DESCRIPTION: SEQ ID NO:8:

CGTTGTAAAA CGGCCAGT                                                                                    1 8

( 2 ) INFORMATION FOR SEQ ID NO:9:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( i x ) FEATURE:
    ( A ) NAME/KEY: misc_feature
    ( B ) LOCATION: 1
    ( D ) OTHER INFORMATION: /note="The N-terminal of this
      sequence has been modified as shown in the
      specification, on page 32, line 36."

( x i ) SEQUENCE DESCRIPTION: SEQ ID NO:9:

GACCTTGGGA ATTCCCCGGG CTGCAGTTTT TTTTTTTTT TTTTTTTTT T                                                5 1

( 2 ) INFORMATION FOR SEQ ID NO:10:

( i ) SEQUENCE CHARACTERISTICS:
    ( A ) LENGTH: 51 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( i x ) FEATURE:
    ( A ) NAME/KEY: misc_feature
    ( B ) LOCATION: 1
    ( D ) OTHER INFORMATION: /note="The N-terminal of this
      sequence has been modified as shown in the
      specification, on page 33, line 18."

( x i ) SEQUENCE DESCRIPTION: SEQ ID NO:10:

TTAATTATCA GTAAAGCTT CCTGTTGCAC TTTGGGGTG AAGGAAAAAC C                                                5 1

We claim:

1. A plurality of monodisperse, superparamagnetic particles, wherein:

each particle comprises (i) superparamagnetic iron oxide dispersed within a polymer particle, (ii) a coating which reduces non specific binding, and (iii) a functional group carried by said coating for bonding a nucleic acid the particles are monodisperse and have a diameter standard deviation of less than 5%, and particles of said plurality carry a plurality of molecules of an oligonucleotide.

2. Particles as claimed in claim 1, wherein a 5'-amino group on said oligonucleotide is covalently bonded to the particle surface via a 5'-amido group formed with a carboxyl group on the particle.

3. Particles as claimed in claim 2 in which the particles have a coating of a polyacrylic or polymethacrylic acid to provide carboxyl groups which form said 5'-amido group by reaction with a 5'-amino group on the oligonucleotide.

4. Particles as claimed in claim 1 in which the oligonucleotide is covalently bonded directly to the particle surface via a 5'-amino group on said oligonucleotide.

5. Particles as claimed in claim 1 in which the oligonucleotide is bonded to the particle surface by a 5'-biotinyl group on said oligonucleotide which bonds to avidin or streptavidin on the particle.

6. Particles as claimed in claim 1 in which the oligonucleotide is covalently bonded to the particle by a 3'-hydroxy group on said oligonucleotide which bonds to hydroxyl on the particle surface.

7. Particles as claimed in claim 1 having a specific gravity in the range 1.1 to 1.8.

8. Particles as claimed in claim 1 in the size range 1 to 10 microns.

9. Particles as claimed in claim 1 in which the oligonucleotide has a chain length in the range 12 to 200 bases.

10. Particles as claimed in claim 1 in which the oligonucleotide is polydT.

11. Particles as claimed in claim 1 wherein said oligonucleotide hybridizes specifically to a DNA or RNA target.

12. Particles as claimed in claim 11 in which the oligonucleotide hybridizes specifically to a conserved region of a family of target nucleic acids.

13. Particles as claimed in claim 1 in which the oligonucleotide comprises a region hybridizing specifically to a target nucleic acid and, joined to the particle, a linker sequence containing a restriction endonuclease restriction site.

14. A method of preparing magnetic particles as claimed in claim 1, wherein monodisperse, superparamagnetic particles carrying functional groups on the surface thereof are reacted with an oligonucleotide carrying one or more functional groups reactive with the functional groups on said particles, whereby said oligonucleotide is bonded to said particles.

15. A process as claimed in claim 14 in which the oligonucleotide is bonded by a reaction or synthesis selected from the group consisting of:

(a) reaction of biotin on the oligonucleotide with avidin or streptavidin on the particle;

(b) reaction of a 5'-amino group on the oligonucleotide with a carboxyl or tosyloxy group on the particle; and (c) direct chemical synthesis of the oligonucleotide on particles carrying hydroxyl or protected hydroxyl groups.

16. A method of immobilizing a target nucleic acid whereby said nucleic acid is contacted in solution with particles as claimed in claim 1 whereby the oligonucleotide thereon hybridizes to a nucleotide sequence on said target nucleic acids, thereby immobilizing said target nucleic acid.

17. A method as claimed in claim 16 in which the target nucleic acid is mRNA and the particles are subsequently magnetically aggregated to a surface and separated from said solution.

18. A method as claimed in claim 16 in which the target nucleic acid when immobilized on said particles is subjected to amplification by the polymerase chain reaction using the oligonucleotide attached to said particles as one of the two primers, further particles carrying said oligonucleotide being present or added subsequently to provide a sufficient amount of the said primer to permit amplification.

19. A method of sequencing single stranded nucleic acids which comprises the steps of:

(a) preparing a plurality of superparamagnetic monodisperse particles wherein each particle comprises (i) superparamagnetic iron oxide dispersed within a polymer particle and (ii) a coating which reduces non-specific binding; and which carries a functional group for bonding a nucleic acid and the particles being monodisperse and having a diameter standard deviation of less that 5%, and particles of said plurality carrying a plurality of moleceles of an oligonucleotide to be sequenced;

(b) either (i) dividing the particles into four aliquots and adding to each aliquot a polymerase, mixed nucleoside triphosphates, a single dideoxynucleoside triphosphate, the latter being different for each aliquot and, a primer, if required, wherein at least one of the primer or nucleoside or dideoxynucleoside is labelled; or (ii) adding to all the particles a polymerase, mixed nucleoside triphosphates, four different dideoxy nucleoside triphosphates each carrying a different label and, a primer, whereby, a series of labelled DNA strands are synthesized each having different chain lengths and ending with a particular dideoxy base, (c) liberating the labelled DNA strands and size fractionating these; and (d) determining the sequence of the nucleic acids.

20. A kit for the detection or isolation of target nucleic acids, comprising:

(a) magnetic particles as claimed in claim 1, and at least one of the following:

(b) a polymerase (c) a reverse transcriptase (d) a restriction endonuclease (e) appropriate buffers (f) dideoxynucleotides some of which may carry, or be adapted to carry a label (g) deoxynucleotides, some of which may carry, or be adapted to carry, a label (h) an oligonucleotide carrying, or adapted to carry, a label (i) a 5'-primer or a 3'-primer, or both, which may be labelled.

* * * * *